United States Patent

Harrison, III

[11] Patent Number: 6,146,139
[45] Date of Patent: Nov. 14, 2000

[54] FORCEPS APPARATUS

[76] Inventor: Louis V. Harrison, III, 412 Tyler Holmes Dr., Winona, Miss. 38967

[21] Appl. No.: 09/323,337
[22] Filed: Jun. 1, 1999
[51] Int. Cl.[7] .................................................. A61C 3/14
[52] U.S. Cl. .............................. 433/159; 606/210; 81/3.8
[58] Field of Search .................................... 433/156, 157, 433/159; 83/426.5, 3.8; 606/210, 205, 207

[56] References Cited

U.S. PATENT DOCUMENTS

| D. 157,104 | 1/1950 | Tuttle et al. | 606/210 |
|---|---|---|---|
| 1,033,942 | 7/1912 | Ruggles | 606/210 |
| 1,537,793 | 5/1925 | Bates | 606/210 |
| 3,306,139 | 2/1967 | Brackett | 606/210 |
| 3,581,745 | 6/1971 | Eller | 606/210 |
| 3,916,910 | 11/1975 | Seeling et al. | 606/210 |
| 3,977,410 | 8/1976 | Huston et al. | 606/210 |
| 4,212,305 | 7/1980 | Lahay | 606/210 |
| 5,156,431 | 10/1992 | Lowe | 606/210 |

Primary Examiner—Todd E. Manahan
Attorney, Agent, or Firm—Gavey, Smith, Nehrbass & Doody, LLC

[57] ABSTRACT

A forceps apparatus having particular utility in the removal of small teeth provides a pair of arms or limbs, each having proximal and distal end portions and a middle portion spaced about midway in between the proximal and distal end portions. Each limb has an inside concave surface and an outer convex surface. The convex surface of each limb is curved to continuously engage the thumb and forefinger of a user when the user places the forceps between the thumb and forefinger. A hinge connects the proximal ends of the limbs together. The distal ends of the limbs provide respective gripping jaw portions that are concavely shaped to conform to and grip a tooth during use. Each limb has a transverse width that varies in between the hinge and the tip. The transverse width of each of the limbs is preferably many times greater at the middle portion of the respective limb than at the tip.

20 Claims, 2 Drawing Sheets

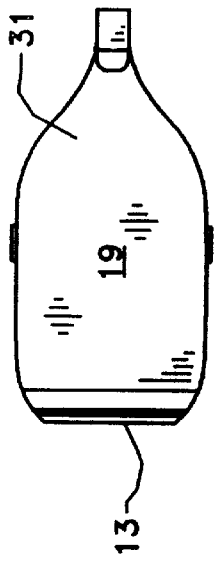
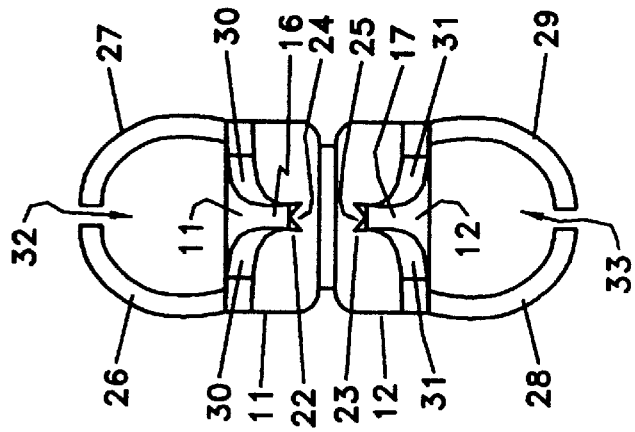
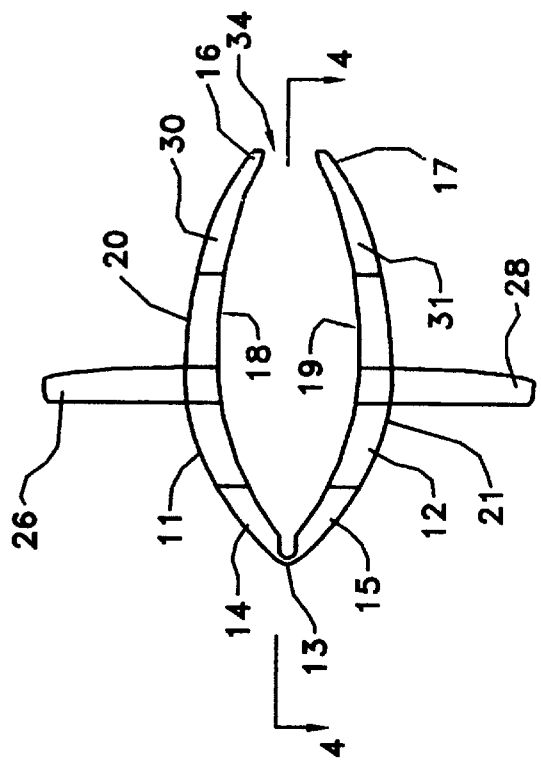

FORCEPS APPARATUS

BACKGROUND OF THE INVENTION

1. Field of the Invention

The present invention relates to dental forceps apparatus, more particularly an improved forceps apparatus having improved utility in the removal of very small teeth from a patient such as the removal of baby teeth from a child. Even more particularly, the present invention relates to an improved forceps apparatus having a pair of limbs which are curved to continuously engage the thumb and forefinger of a user when the user places the forceps in between the thumb and forefinger, the mid-portion of each limb being much wider than the tip portion. Each limb carries a ring that fits the user's thumb or forefinger.

2. General Background of the Invention

Medical forceps have been produced in a number of differing configurations. The present invention is directed to an improved forceps having particular utility in the removal of very small teeth from children, such as baby teeth.

Patents have issued that are directed to the concept of removal of small teeth or loose teeth from a patient. As an example, the Osborn U.S. Pat. No. 2,674,800, entitled "Loose Tooth Remover" relates to the removal of loose baby teeth and aims to provide a simple, effective and safe device for the removal of such teeth. The Osborn Patent is operated by gripping a pair of space apart finger loop portions that operate the jaws much in the same fashion as a user would operate a common pair of scissors.

A plastic forceps apparatus is the subject of U.S. Pat. No. 3,265,068, issued to Holohan. In the Holohan patent, the limbs of the forceps are linear, providing flat upper and lower surfaces of each limb.

The Visser U.S. Pat. No. 5,522,290 provides a pair of compliant pliers that include an endless loop, a top jaw appended to the endless loop, and a bottom jaw appended to the endless loop. The endless loop includes in series a top grip handle, a spring segment, a bottom grip handle, and a compliance strip interconnecting the top and bottom grip handles. A rolling surface on the top grip handle rolls on a contact portion of the bottom grip handle. The rolling action causes the compliant strip to flex which causes the top and bottom jaws to move toward one another. The endless loop provides a built in automatic spring and enhances lateral stability.

The Lane U.S. Pat. No. 2,944,341 discloses a dental forceps designated as root forceps.

The Klein U.S. Pat. No. 3,834,026 discloses a crown remover in the form of pliers having a pair of opposed arm members pivotally connected to define on one side of a pivot a pair of opposed jaws wherein the improvement resides in a resilient deformable gripping surface on the surface of the jaws generally contoured to coincide with a side surface of a crown.

The Lukase U.S. Pat. No. 5,057,016 discloses a dental forceps that includes a pair of teeth having removable cushioning and gripping inserts for comformingly gripping and frictionally retaining a respective dental prosthetic device, such as a crown or bridge, to be removed without opposing stress concentrations sufficient to mar or damage the dental prosthetic device.

The Linder U.S. Pat. No. 3,898,738 discloses a dental instrument that is comprised of a scissors-like device having opposed egg shaped padded members engagable on opposite sides to grasp a cast metal or porcelain crown for seating and removal during try in and cementation procedures.

The Lukas U.S. Pat. No. 5,044,954 discloses a pair of dental forceps configured for anterior premolar or molar teeth that includes a pair of jaws having removable cushioning and gripping inserts for conformingly gripping and frictionally retaining respective dental prosthetic device such as a crown to be removed without imposing stress concentrations sufficient to mar or damage the dental prosthetic device.

BRIEF SUMMARY OF THE INVENTION

The present invention provides an improved forceps apparatus having particular utility in the removal of small teeth (eg. Baby teeth. The apparatus includes a pair of limbs, each limb having proximal and distal end portions and a middle portion spaced about midway in between the proximal and distal end portions, each limb having an inside concave surface and an outer convex surface.

The convex surface of each limb is curved to continuously engage the thumb and forefinger of a user when the user places the forceps between the thumb and forefinger. A hinge connects the proximal ends of the limbs together.

The distal ends of the limbs provide respective gripping jaw portions that are concavely shaped and to conform and to grip a tooth during use.

Each limb has a transverse width that varies in between the hinge and the tip.

The transverse width of each of the limbs is many times greater at the middle portion than at the respective tip portions of the limbs.

The limbs are preferably of the same length, preferably between about 1.5 and 2.5 inches in length.

The hinge and limbs are configured as an integral unit that spaces the jaws automatically a distance of at least 0.2 inches apart when the forceps are not being gripped.

The apparatus includes a pair of rings supported respectively on the pair of limbs, each ring being sized and shaped to support the thumb or finger of a user.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 3 is a side view of the preferred embodiment of the apparatus of the present invention;

FIG. 4 is a top view of the preferred embodiment of the apparatus of the present invention; and FIG. 5 is an end view of the preferred embodiment of the apparatus of the present invention.

DETAILED DESCRIPTION OF THE INVENTION

Figure 1:
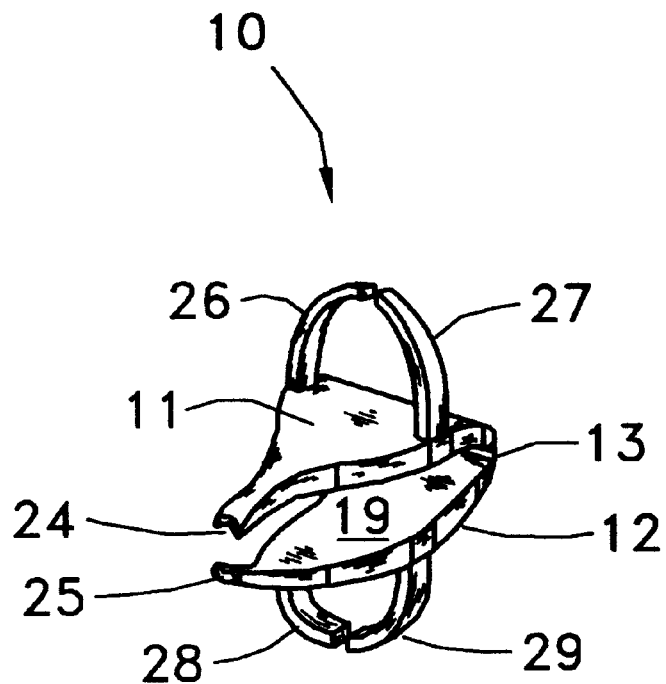
FIG. 1 is a perspective view of the preferred embodiment of the apparatus of the present invention.
Figure 2:
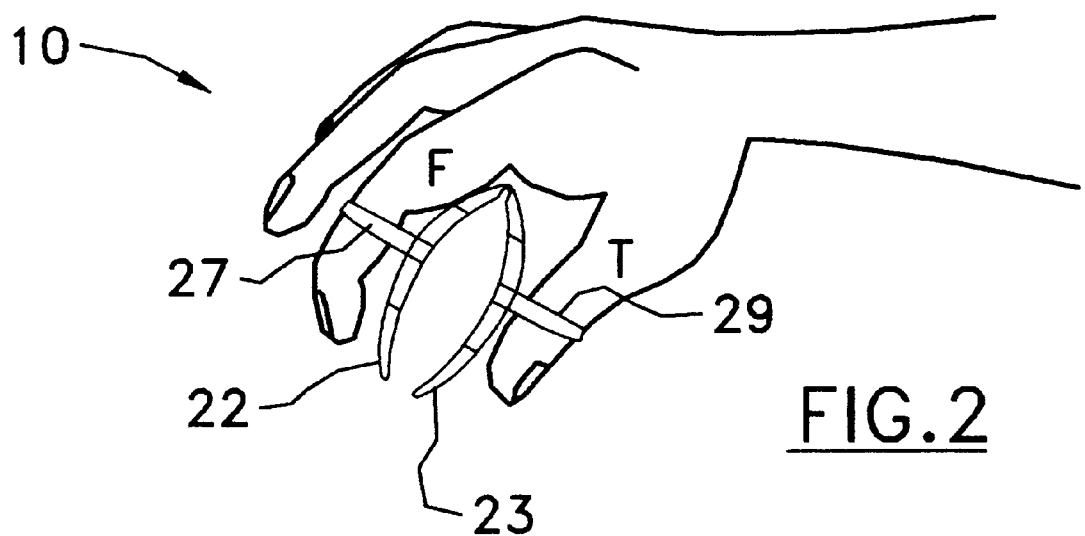
FIG. 2 is a perspective view of the preferred embodiment of the apparatus of the present invention shown during use when gripped by a user.

Forceps apparatus 10 is shown generally in FIGS. 1–5 as including a pair of arms or limbs 11, 12 connected by hinge 13. The combination of arms 11, 12 and hinge 13 can be a one piece injection molded construction. The hinge 13 and arms 11, 12 can be configured so that a gap 34 is present between the jaws 22,23 that are at the distal 16, 17 ends of arms 11, 12. The gap 34 is preferably about a quarter of an inch.

Arms 11, 12 have respective proximal ends 14, 15 and respective distal ends 16, 17. The distal ends 16, 17 communicate with hinge 13.

Each arm 11, 12 is curved to fit the thumb and forefinger respectively of a user as shown in FIG. 1. The radius of curvature of each of the concave surfaces 18, 19 of the respective arms 11,12 is preferably between about 1.5 and 3 inches. Arm 11 thus provides concave surface 18 and convex surface 20. Similarly, arm 12 provides concave surface 19 and convex surface 21. Each arm 11, 12 provides a distal end portion 16, 17 respectively having a jaw 22, 23 respectively as shown in FIGS. 3 and 5.

Each jaw 22, 23 has a concavity that faces the concavity of the opposing jaw. In FIG. 5, the jaw 22 has a concavity 24 that faces the concavity 25 of jaw 23. When the user forces the arms 11, 12 together, these concavities 24, 25 converge to grip a small tooth such as a baby tooth making removal simple and quick. The concavities 24, 25 are shaped to conform to a small tooth to be removed.

In order to assist the user in gripping the arms 11, 12 there are a pair of opposed receptacles in the form of curved struts as shown in FIG. 5. Curved struts 26, 27 define a receptacle opening 32 that can be receptive of a user's forefinger F. The curved struts 28, 29 define a receptacle opening 33 that is receptive of a user's thumb T. The curvature of surface 20 is shaped to continuously engage a user's forefinger during use (see FIG. 2).

Each arm 11, 12 is much wider at the mid-section, near the curved struts 26–29 than at the distal tip 16, 17 as shown in FIG. 5. This provides for a wide surface over a majority of the length of each arm 11, 12 that is much larger in width than the width of the jaw 22, 23 at distal ends 16, 17. The width of each arm 11, 12 next to the struts 26–29 at the mid section of each arm 11, 12 can be about 0.75–1.5 inches. Conversely, the width of each of the jaws 22, 23 at distal ends 16, 17 respectively is about 0.1–0.2 inches in width.

As shown in FIG. 4, the arms are widened over a majority of the length and narrow to the jaws only at the very distal end. In that regard, each arm 11, 12 provides a tapered section 30, 31 respectively that interfaces between the widest portion of arms 11, 12 and the distal tips at jaws 22, 23.

PARTS LIST

The following is a list of parts and materials suitable for use in the present invention:

| Part List | |
|---|---|
| 10 | forceps apparatus |
| 11 | arm |
| 12 | arm |
| 13 | hinge |
| 14 | proximal end |
| 15 | proximal end |
| 16 | distal end |
| 17 | distal end |
| 18 | concave surface |
| 19 | concave surface |
| 20 | convex surface |
| 21 | convex surface |
| 22 | jaw |

| -continued | |
|---|---|
| Part List | |
| 23 | jaw |
| 24 | concavity |
| 25 | concavity |
| 26 | curved strut |
| 27 | curved strut |
| 28 | curved strut |
| 29 | curved strut |
| 30 | tapered section |
| 31 | tapered section |
| 32 | opening |
| 33 | opening |
| 34 | gap |
| F | finger |
| T | thumb |

The foregoing embodiments are presented by way of example only; the scope of the present invention is to be limited only by the following claims.

What is claimed is:

1. A forceps apparatus comprising:
   a) a pair of curved limbs, each limb extending along longitudinal lines and having proximal and distal end portions and a middle portion spaced about midway in between said proximal an distal end portions, and each limb having an inside concave surface and an outer convex surface, the convex surfaces being each curved to continuously engage the thumb and forefinger of a user when the user places the forceps between the thumb and forefinger;
   b) a hinge that connects the proximal ends of the limbs together;
   c) the distal ends of the limbs providing respective gripping jaw portions that are concavely shaped to conform to and grip a tooth during use each gripping jaw portion having a concave surface that extends transversely relative to its limb;
   d) each limb having a transverse width that varies in between the hinge and the tip;
   e) the transverse width of each of the limbs being many times greater at the middle portion of each respective limb than at the tip of each respective limb.

2. The forceps apparatus of claim 1 wherein the limbs are of the same length.

3. The forceps apparatus of claim 1 wherein each limb is about 1.5–2.5 inches in length.

4. The forceps apparatus of claim 1 wherein each limb is about 2 inches in length.

5. The forceps apparatus of claim 1 wherein the hinge and limbs are configured as an integral unit that spaces the jaws a distance of at least 0.2 inches apart when the forceps are not being gripped.

6. The forceps apparatus of claim 1 further comprising a pair of transversely extending rings supported respectively by the pair of limbs, each ring being sized and shaped to support the thumb or finger of a user that is aligned with a limb.

7. A forceps apparatus comprising:
   a) a pair of limbs, each limb having proximal and distal end portions and a middle portion spaced about midway in between said proximal an distal end portions, and each limb having an inside concave surface and an outer convex surface, the convex surface being curved to continuously engage the thumb and forefinger of a user when the user places the forceps between the thumb and forefinger;

b) a hinge that connects the proximal ends of the limbs together;

c) the distal ends of the limbs providing respective gripping jaw portions that are concavely shaped to conform to and grip a tooth during use;

d) each limb having a transverse width that varies in between the hinge and the tip;

e) the transverse width of each of the limbs being many times greater at the middle portion of each respective limb than at the tip portion of the limb f) a pair of receptacles respectively supported by the convex surface of a limb, each receptacle being sized and shaped to support the thumb or finger of a user.

8. The forceps apparatus of claim 7 wherein each receptacle is comprised of a pair of curved struts that extend away from the convex surface of the limbs.

9. The forceps apparatus of claim 7 wherein each receptacle is comprised of a curved member that extends away from the convex surface of the limbs, the curved member defining a plane that is generally perpendicular to a plane defined by intersecting the longitudinal centerlines of each limb.

10. The forceps apparatus of claim 7 wherein each receptacle is comprised of a pair of curved struts that extend away from the convex surface of the limbs.

11. The forceps apparatus of claim 7 wherein each receptacle is comprised of a curved member that extend away from the convex surface of the limbs, the curved member defining a plane that is generally perpendicular to a plane defined by intersecting the longitudinal centerlines of each limb.

12. A forceps apparatus comprising:

a) a pair of curved limbs, each limb having proximal and distal end portions and a middle portion spaced about midway in between said proximal an distal end portions, and each limb having an inside concave surface with a radius of curvature of between about 1.5 and 3 inches and an outer convex surface, the convex surface being curved to continuously engage a majority of the length of the thumb and forefinger of a user when the user places the forceps between the thumb and forefinger;

b) a hinge that connects the proximal ends of the limbs together;

c) each limb having a ring that generally encircles the users thumb of forefinger during use;

d) the distal ends of the limbs providing respective gripping jaw portions that are concavely shaped to conform to and grip a child's tooth during use, each gripping jaw portion having a concave surface that extends transversely relative to its limb;

e) each limb having a transverse width that varies in between the hinge and the tip; and f) the transverse with of each of the limbs being many times greater at the middle portion of the respective limb than at the tip.

13. The forceps apparatus of claim 12 wherein the limbs are of the same length.

14. The forceps apparatus of claim 12 wherein each limb is about 1.5–2.5 inches in length.

15. The forceps apparatus of claim 12 wherein each limb is about 2 inches in length.

16. The forceps apparatus of claim 12 wherein the hinge and limbs are configured as an integral unit that spaces the jaws a distance of at least 0.2 inches apart when the forceps are not being gripped.

17. The forceps apparatus of claim 12 further comprising a pair of rings transversely extending supported respectively by the pair of limbs, each ring being sized and shaped to support the thumb or finger of a user.

18. The forceps apparatus of claim 12 further comprising a pair of receptacles respectively supported by the convex surface of a limb, each receptacle being sized and shaped to support the thumb or finger of a user.

19. A forceps apparatus comprising:

a) a pair of limbs, each limb having proximal and distal end portions and a middle portion spaced about midway in between said proximal an distal end portions, and each limb having an inside concave surface and an outer convex surface, the convex surface being curved to continuously engage the thumb and forefinger of a user when the user places the forceps between the thumb and forefinger;

b) a hinge that connects the proximal ends of the limbs together;

c) the distal ends of the limbs providing respective gripping jaw portions that are concavely shaped to conform to and grip a tooth during use;

d) each limb having a transverse width that varies in between the hinge and the tip;

e) the transverse width of each of the limbs being many times greater at the middle portion of each respective limb than at the tip portion of the limb; and f) wherein each limb is between about 1.5 and 2.5 inches in length and has a curved portion with a radius of curvature of between about 1.5 and 3.0 inches.

20. A forceps apparatus comprising:

a) a pair of longitudinally extending, curved limbs, each limb having proximal and distal end portions and a middle portion spaced about midway in between said proximal an distal end portions, and each limb having an inside concave surface and an outer convex surface, the convex surface being curved to continuously engage a majority of the length of the thumb and forefinger of a user when the user places the forceps between the thumb and forefinger;

b) a hinge that connects the proximal ends of the limbs together;

c) each limb having a transverse ring that generally encircles the users thumb or forefinger during use when the user's thumb and forefinger continuously engage a majority of the length of the limb;

d) the distal ends of the limbs providing respective gripping jaw portions that are concavely shaped to conform to and grip a child's tooth during use;

e) each limb having a transverse width that varies in between the hinge and the tip; and f) the transverse with of each of the limbs being many times greater at the middle portion of the respective limb than at the tip.

\* \* \* \* \*